United States Patent [19]
Kinanen

[11] 4,419,764
[45] Dec. 6, 1983

[54] SLIT COLLIMATOR IN A PANORAMIC X-RAY APPARATUS

[75] Inventor: Ilmari Kinanen, Espoo, Finland

[73] Assignee: Instrumentarium Oy, Helsinki, Finland

[21] Appl. No.: 304,160

[22] Filed: Sep. 21, 1981

[30] Foreign Application Priority Data

Sep. 22, 1980 [FI] Finland .............................. 802988

[51] Int. Cl.³ .......................... A61B 6/14; G21K 1/02

[52] U.S. Cl. .................................... 378/153; 378/150; 378/40

[58] Field of Search ................. 378/150, 151, 153, 39, 378/40

[56] References Cited

U.S. PATENT DOCUMENTS

| | | | |
|---|---|---|---|
| 3,275,831 | 9/1966 | Martin | 378/153 |
| 3,411,000 | 11/1968 | Schliephake | 378/153 |
| 4,277,685 | 7/1981 | Covic et al. | 378/150 |

FOREIGN PATENT DOCUMENTS

| | | | |
|---|---|---|---|
| 557150 | 9/1943 | United Kingdom | 378/150 |

*Primary Examiner*—Alfred E. Smith
*Assistant Examiner*—T. N. Grigsby
*Attorney, Agent, or Firm*—Andrus, Sceales, Starke & Sawall

[57] ABSTRACT

A slit collimator for use in a panoramic X-ray apparatus for the collimation of X-rays into a narrow fan-like beam. The collimation is achieved by means of a collimator slit formed in a trunion which is rotatable about its longitudinal axis and by rotating the trunion the effective radiation-penetrable size of the slit is varied.

7 Claims, 4 Drawing Figures

SLIT COLLIMATOR IN A PANORAMIC X-RAY APPARATUS

The present invention relates to a slit collimator in a panoramic X-ray apparatus for the collimation of the X-ray beam to a narrow fan-like beam of rays in one direction.

BACKGROUND OF THE INVENTION

The collimator slit is generally narrow and of equal width. An exception is a V-shaped slit as disclosed in the Finnish Patent Publication No. 54856. However, it is preferable in various applications of radiography that the width and/or shape of the slit could be changed, case by case by means of presetting or by continuous adjustment during radiography. A problem is, however, to effect the adjustment accurately and symmetrically on both edges of the slit in order to maintain accurate concentration and alignment of the beam of rays.

SUMMARY OF THE INVENTION

The invention seeks to achieve the above object and to resolve the problem by an apparatus which is simple in design and reliable in operation.

For this object, a slit collimator of the invention is characterized in that the collimation of said beam of X-rays is substantially achieved by means of a collimator slit formed on means, e.g. on a trunnion, turntable around its longitudinal axis, in such a manner that, by turning said means, the effective, radiation penetrable size of the slit is changed, and that the trunnion is centrally journalled with respect to said collimator slit. Turning of said trunnion will effect symmetric adjustment of both edges of the slit in regard to the plane of symmetry of the wider direction of a beam passing through said slit.

The present solution also offers a simple possibility of re-shaping a beam of rays, effected e.g. in such a manner that the cross-section of said trunnion varies in different parts of its length. For example, by means of a conical trunnion, it is possible to provide a V-shaped beam of rays whose V-angle changes as the trunnion is turned.

A lever for turning the trunnion can be provided with a measuring scale, according to which the size of the slit can be present. Turnings motion of the trunnion can also be effected by means of an electric actuator, such as a galvanometer, controlled e.g. on the basis of measurement of the amount of radiation penetrated through a patient.

DESCRIPTION OF THE DRAWINGS

In the following the invention is explained more in detail with reference to the accompanying drawings, in which.

DESCRIPTION OF THE ILLUSTRATED EMBODIMENT

Figure 1:
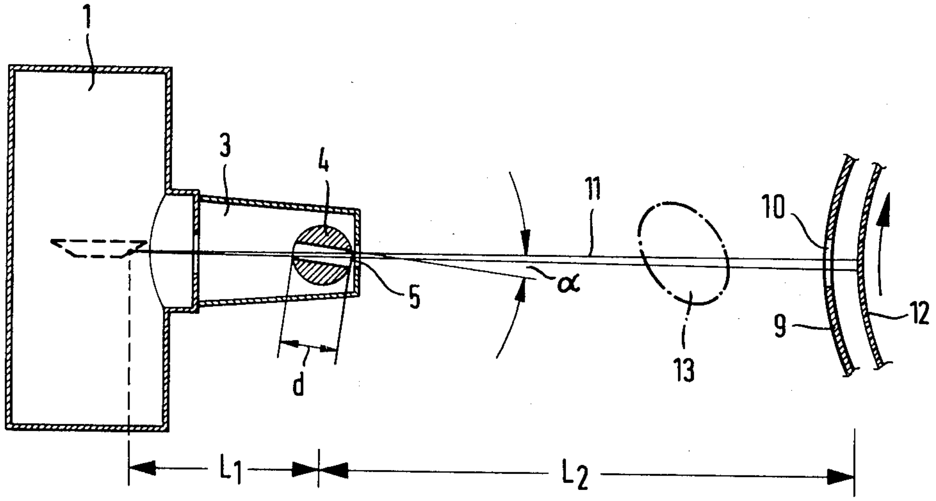
FIG. 1 shows schematically a slit collimator according to the invention in an X-ray apparatus. For illustrative reasons, proportions of the figure do not comply with reality.

The X-radiation emitting from an X-ray tube 1 is first confined by a radiation absorbing disc 2 mounted on the forward end of a collimator tube. The actual confining or trimming of a beam of rays is effected by an apparatus mounted on the rear end of a collimator tube 3, said apparatus, according to the invention, consisting of a trunnion 4 which is supported by its ends by bearings 13 so as to be turnable around its longitudinal axis. Trunnion 4 is provided with a longitudinally extending slit 5. When turning trunnion 4 around its longitudinal axis, the effective or radiation penetrable width of slit 5 can be changed. Since trunnion 4 turns around its central longitudinal axis which conjoins the plane of symmetry of the wider direction of a beam of rays 11, the definition or trimming of beam 11 occurs symmetrically on both sides, whereby the direction of beam 11 does not change. Thereafter, the beam of rays 11 passes through an object 13 to be radiographed and a fixed slit 10, made in a secondary radiation eliminating plate 9, on to a film 12. Slit 10 is wider than the beam of rays 11.

If the diameter of trunnion 4, i.e. the length of slit 5 in alignment with beam 11, is indicated as "d" and the angle of turning of said trunnion is indicated as "$\alpha$", the initial width of the beam of rays in slit 5 is a function of turning angle $\alpha$ according to the following formula $$\text{initial width of beam} = \Delta_{max} - d \sin \alpha,$$

in which $\Delta_{max}$ is maximum width of the slit. Width of the beam on the film is thus $((L1+L2)/L1)\times$ initial width in the collimator slit, when L1 is the distance from focus to collimator slit and L2 from collimator slit to film.

Figure 2:
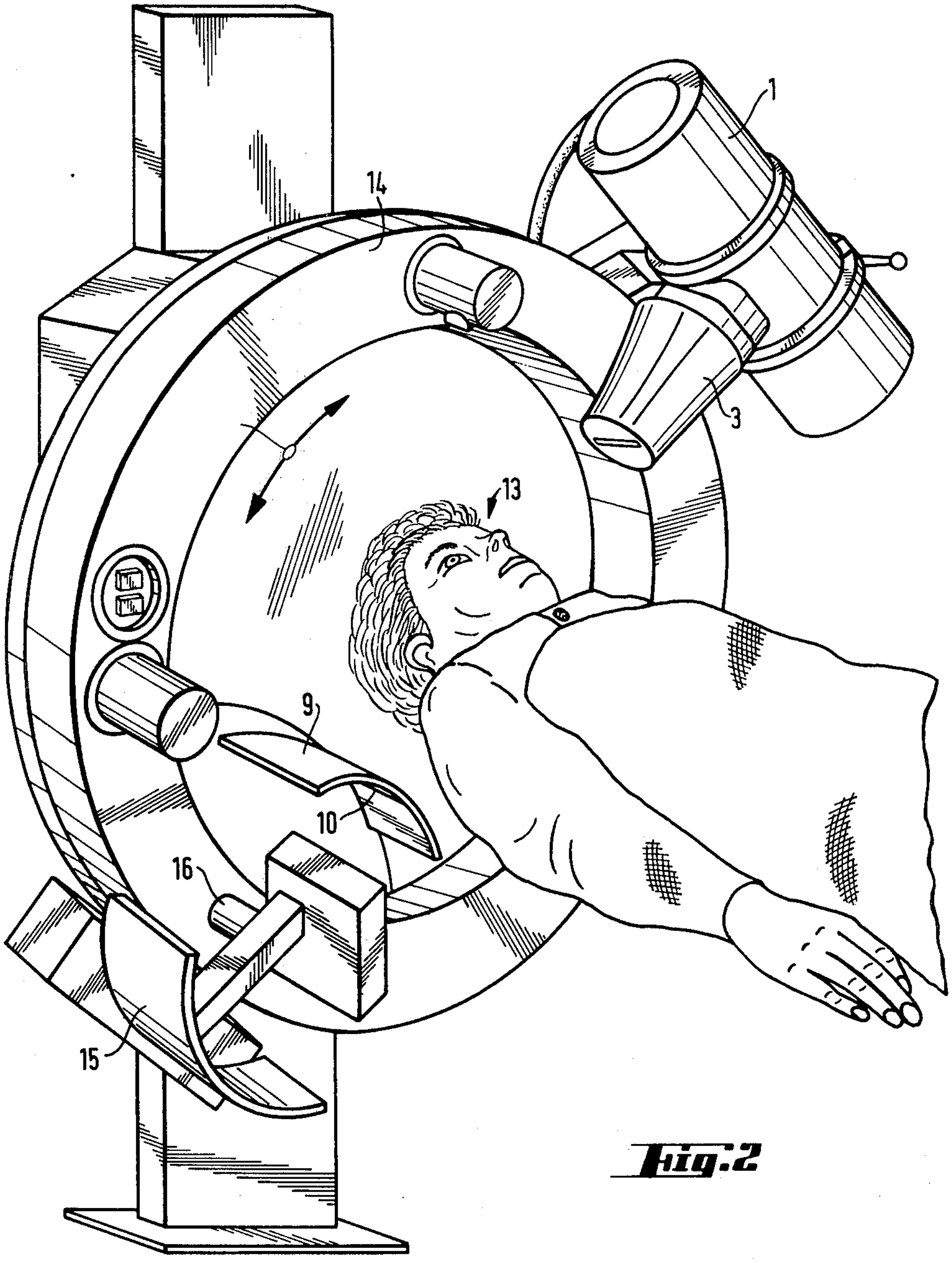
FIG. 2 is a perspective view of a panoramic X-ray apparatus in which a slit collimator according to the invention is employed.

The present slit collimator has a particular practical significance in connection with a panoramic X-ray apparatus illustrated in FIG. 2. In this apparatus, an X-ray tube 1, together with its slit collimator 3, is mounted on the rim of a disc-shaped rotary member 14. Said rotary member 14 is journalled to be rotatable around its central axis. The rim of said rotary member 14, diametrally opposite to slit collimator 3, is provided with a film holder 15 which can be rotated around a pivot 16 to thereby move the film past slit 10 in plate 9. In addition, said rotary member 14 is arranged to be movable in vertical direction during radiography. By selecting the rotational velocity of said rotary member 14, the speed and the travel of its vertical movement as well as the rotational velocity of said film holder 15 in certain manner, a so-called panoramic X-ray image is obtained on the film in holder 5 of a certain layer of the object 13 to be radiographed.

Figure 4:
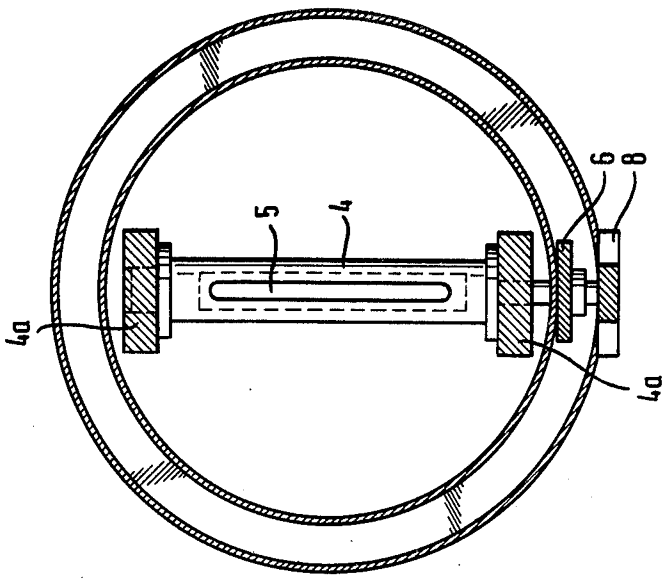
FIG. 4 shows section IV—IV of the slit collimator of FIG. 3 seen in the direction of the beam of rays.
Figure 3:
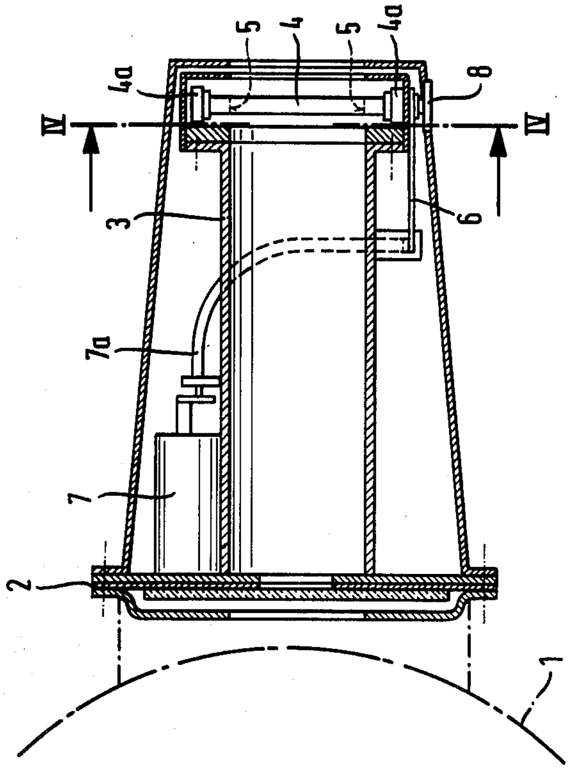
FIG. 3 shows a more detailed view of an embodiment of a slit collimator according to the invention in a longitudinal section.

A more detailed design of the slit collimator is now described with reference to FIGS. 3 and 4. Mounted on the end of trunnion 4 is a turning lever 6 as well as a measuring scale 8. Turning lever 6 can be manually operated but, alternatively, it can be turned by means of a galvanometer or a like actuator 7 which achieves quick setting of the size of slit 5 e.g. on the basis of measurement of the amount of radiation penetrated through a patient. It is also possible to make the size of slilt 5 change during the radiography according to a predetermined program depending on the amount of radiation required by the object to be radiographed at a given moment.

In the embodiment illustrated, an electric actuator 7 is connected to turning lever 6 by means of a wire *7a*. In an alternative embodiment, trunnion 4 ban be arranged to be turn by a measuring scale wheel 8, mounted directly on its end, or by means of a galvanometer. The measuring scale indicates e.g. width of the beam of rays on the film and the indication can also be effected by means of an electric display device.

Particular advantages of the present apparatus include e.g. accuracy, symmetry and quickness of the adjustment while, at the same time, the solution is constructionally simple.

I claim:

1. A slit collimator in a panoramic tomography X-ray apparatus for the collimation of an X-ray beam to a narrow fan-like beam and for controlling the tomographic layer thickness to be imaged, said collimator including a rotatable member provided with a collimating slit of substantial length relative to its width, said collimating slit allowing radiation penetration through said member, and rotating means for rotating said member around its longitudinal axis to at least two radiation penetration positions, wherein said slit has different effective widths to thereby control the radiation penetration through said member, said member being centrally journalled with regard to the width of said collimating slit.

2. A slit collimator as claimed in claim 1, wherein said rotatable member is a trunion.

3. A slit collimator as claimed in claim 2, wherein the cross-section of said trunion is variable in longitudinal direction.

4. A slit collimator as claimed in claim 2, wherein said trunion is cone-shaped.

5. A slit collimator as claimed in claim 1, wherein said rotatable member includes a measuring-scale.

6. A slit collimator as claimed in claim 1, wherein electric operating means is provided for rotating said rotatable member.

7. A slit collimator as claimed in claim 6, wherein said electric operating means is arranged to be controlled by measuring the amount of radiation that penetrates the patient to be radiographed.

* * * * *